(12) United States Patent
Russwurm et al.

(10) Patent No.: US 8,791,826 B2
(45) Date of Patent: Jul. 29, 2014

(54) METHOD AND DEVICE FOR FIRE DETECTION IN ENCLOSED ENVIRONMENTS

(75) Inventors: Manfred Russwurm, Bad Schwartau (DE); Torsten Westphal, Lübeck (DE); Thomas Mendle, Timmendorferstrand (DE); Olaf Klischat, Elmenhorst (DE); Bernd Ziems, Zarpen (DE); Hauke Dittmer, Fehmarn (DE); Kurt Lenkeit, Sülfeld (DE)

(73) Assignee: Minimax GmbH & Co. KG, Bad Oldesloe (DE)

( * ) Notice: Subject to any disclaimer, the term of this patent is extended or adjusted under 35 U.S.C. 154(b) by 325 days.

(21) Appl. No.: 13/304,807

(22) Filed: Nov. 28, 2011

(65) Prior Publication Data
US 2012/0133518 A1  May 31, 2012

(51) Int. Cl.
*G08B 21/00* (2006.01)
*G08B 17/10* (2006.01)
*G06F 9/455* (2006.01)

(52) U.S. Cl.
USPC ........... 340/607; 340/609; 340/610; 340/626; 340/628; 340/630; 703/23

(58) Field of Classification Search
None
See application file for complete search history.

(56) References Cited

U.S. PATENT DOCUMENTS

| 4,701,193 | A | * | 10/1987 | Robertson et al. | 96/380 |
| 5,755,250 | A | * | 5/1998 | Cole | 137/78.5 |
| 6,052,058 | A | * | 4/2000 | Knox | 340/607 |
| 7,777,633 | B2 | * | 8/2010 | Knox et al. | 340/607 |
| 8,314,710 | B2 | * | 11/2012 | Knox et al. | 340/607 |
| 2009/0002182 | A1 | * | 1/2009 | Knox et al. | 340/628 |
| 2012/0154161 | A1 | * | 6/2012 | Knox et al. | 340/628 |

FOREIGN PATENT DOCUMENTS

| DE | 19781749 T1 | 4/2001 |
| DE | 10125687 A1 | 12/2002 |
| EP | 1542188 B1 | 8/2006 |

* cited by examiner

*Primary Examiner* — Julie Lieu
(74) *Attorney, Agent, or Firm* — Harness, Dickey & Pierce, P.L.C.

(57) ABSTRACT

A method for fire detection in enclosed environments (1) subject to explosion protection regulations out of which an air-dust mixture is filtered while the concentration of dust of the air-dust mixture is lowered to under the explosion limit by a filter (2) and the aspirated air-dust mixture is checked for burning characteristics and if appropriate a fire alarm is triggered, in which the function of the filter (2) is monitored, the fire detection is carried out by use of an aspirating smoke detector system (7) not approved for use in potentially explosive areas but instead is deployed outside the ex-zone and if the filter (2) is destroyed a signal processing unit (15, 15.1) of a malfunction monitoring sensor (14) generates a signal which initiates a subsequent action preventing aspirated air-dust mixture with an elevated concentration of dust from entering the aspirating smoke detector system (7).

15 Claims, 6 Drawing Sheets

METHOD AND DEVICE FOR FIRE DETECTION IN ENCLOSED ENVIRONMENTS

CROSS-REFERENCE TO RELATED APPLICATIONS

This application claims the benefit and priority of German Patent Application No. 10 2010 052 611.8, filed Nov. 29, 2010. The entire disclosure of the above application is incorporated herein by reference.

FIELD

The present disclosure relates to a method for fire detection in enclosed environments.

BACKGROUND

Device and method for fire detection in enclosed environments are suitable for storage rooms, silos, bunkers, and other enclosures, which are, among other things, subject to regulations on explosion protection and from which air is aspirated, checked for typical fire criteria and, if necessary, a fire alarm is triggered.

The present disclosure is especially suitable for enclosed environments such as silos or bunkers for combustible and/or dust forming bulk goods or storage areas for combustible materials from which air samples have to be taken for the purpose of using fire parameters to generate a fire alarm.

Enclosed environments in the sense of the present disclosure can be silos or bunkers as well as other storage areas and transport areas which are subject to explosion protection requirements and in which easily combustible material and dust forming bulk goods such as wood shavings, wood chips, wood pellets, grain, powdered fodder, fertilizer, or other such goods are stored or transported. An explosive air-dust mixture can form due to an appropriately high concentration of dust from these materials. Sources of ignition can then be, for instance, warm or hot parts or surfaces. In the following sections these enclosed environments are also referred to as storage areas. These storage areas/enclosed environments, which are subject to regulations for protection against explosion, are also referred to in the following sections as "ex-zones". In the following sections, "dust" is understood to denote small particles of the materials which are being stored or transported/poured.

Discharge systems, conveyor belts, or processing devices are the primary potential sources of ignition in this context. Through friction or overheating of material being conveyed in the region of the discharge worm drive a deep lying fire can start in a silo or a storage area without being noticed. Ignition sources introduced from outside through the entry opening also constitute a fire hazard. In addition, spontaneous combustion can occur through biological decay processes in piled up materials. A smoldering fire that starts in this way can spread to the surface of the piled up material and, as a result of the access to oxygen, quickly develop into an open fire which destroys the entire storage area or machinery. The difficulty of detecting incipient fires in storage areas, bunkers, or silos is due to the fact that there is often a high proportion of fine dust and carbon monoxide or high relative humidity. Serious problems exist in such ex-zones regarding early detection of fires. Conventional fire detection systems without any technical modifications and without approval for use in ex-zones are not appropriate for use here.

Fire detection systems such as aspirating smoke detector systems with sensors/detectors for detecting fires which are installed to detect fires in ex-zones are required to satisfy the requirements for protection against explosions such as the set of standards EN 60079 or IEC 60079 or the appropriate national requirements such as NEC 500 to NEC 516. Such systems are not permitted to contain any parts which could become so hot that they constitute ignition sources.

Devices which meet these requirements are tested and approved by appropriate national certifying agencies. They are then recognized as devices or machines with ex-approval for specific classified ex-zones such as zones 20, 21 or 22. Devices with ex-approval are technically more complicated and are more costly in comparison with standard machines.

In EP 1 542 188 B1 a device and a method for detecting incipient fires is described according to which samples of air are continuously extracted from spaces or from electrical devices and tested for fire detection characteristics. In order to direct the air flow to be extracted, the aspirator opening must have a specified size and shape.

The filter is for keeping dust concentrations low. No provision is made for monitoring the filter for defects or the air flow for exceeding the explosion limit.

DE 197 81 749 T5 describes a system for monitoring the functioning of the dust filter of a fire detection system in areas which are not potentially explosive for blockage of the filter where, if a specified threshold value is exceeded, a warning signal is generated after which the filter is replaced.

DE 101 25 687 B1 describes a device for detecting fire sources or gas contamination in one or more monitored spaces which has a main detector for detecting a fire parameter value or a gas contamination level which is connected by means of an aspirating unit with a pipe fitted with an intake opening which is required in every space being monitored.

The devices described above are not suitable, nor are they permitted, in particular for cost-effective fire detection in enclosed environments which are subject to explosion protection regulations.

For fire detection equipment such as aspirating smoke detector systems without ex-approval, which extract and analyze air from such enclosed environments, it must be ensured that dust concentrations of the aspirated air-dust mixture sucked in the aspirating smoke detector system are below the limits of the maximum allowable concentration for a potentially explosive atmosphere.

SUMMARY

Consequently, the purpose of the present disclosure is to develop a method and a device for detecting fires in enclosed environments which satisfies the explosion protection regulations without an explosive air-dust mixture entering the fire detection system while also preventing transfer of the explosive atmosphere from the ex-zone into the fire detection system and enabling the use of cost-effective fire detection systems which do not satisfy the requirements for potentially explosive areas.

The solution in this disclosure proposes a method and a device for detecting fires in enclosed environments such as material warehouses, silos, bunkers, or similar structures which are subject to the requirements for prevention of explosions and from which an air-dust mixture is extracted which can contain burning characteristics in the air flow.

"Burning characteristics" are understood to be all indicators such as smoke, heat and flame radiation as well as combustion gases which indicate an incipient or actually burning fire. They are derived from the measurement of physical variables such as temperature, electromagnetic radiation, light scattering in smoke aerosols, or evidence of combustion gases such as CO, NOx or long chain carbohydrates or other substances indicating a smoldering fire.

Aspiration of the air-dust mixture is carried out by a smoke aspiration system which is not approved for use in ex-zones.

An aspirating smoke detector system is a fire detection system which extracts air from an area that is to be monitored. It contains at least one, as a rule several sensors for fire detection. It may also contain combustion gas sensors. In addition, among other things, components for monitoring the air flow and for generating an alarm signal, as well as a signal processing unit and an aspirator are elements of the aspirating smoke detector system. Instead of an aspirator a pump can also be used in the system.

Aspirators or pumps can also be operated outside the aspirating smoke detector system.

An air-gas mixture is extracted from the monitored enclosed environments which constitute an ex-zone by means of a suction pipe into an aspirating smoke detector system and passed through a filter. The purpose of the filter is to reduce the dust concentration in the dust-air mixture sucked into the aspirating smoke detector system below the explosive level.

Decisive for this disclosure is that a filter monitoring unit with a malfunction monitoring sensor is located between the storage area for combustible materials (ex-zone) and the aspirating smoke detector system, which is not approved for use in explosion risk areas and is positioned in the non-ex-zone where there is no danger of an explosion. Preferably, the malfunction monitoring sensor should be positioned at the filter or in its immediate vicinity.

The malfunction monitoring sensor continuously monitors the operability of the filter. A malfunction exists in the filter/filters if, for example, the concentration of dust in the airstream beyond the filter is inadmissibly high. This can occur because of leaks in the filter or because the filter is destroyed. In the following sections this will be referred to as destruction of the filter.

The filter monitoring unit measures and records increases in dust concentration in the aspirated air stream behind the filter and generates a malfunction signal if the measured dust concentration values exceed specified threshold concentration values or threshold slope (gradient) values.

The malfunction monitoring sensor is connected to a signal processing unit which contains stored threshold values for ignitable dust concentrations and/or advance warning threshold values and/or slope (gradient) values.

The term "signal processing unit" denotes a signal-processing and control unit with a memory. Preferably, this is the signal processing unit of the aspirating smoke detector system. It can also be integrated into the filter monitoring unit separate from the aspirating smoke detector system.

The threshold value for an explosive wood dust concentration for instance is more than 30 g of dust per cubic meter of air with the corresponding range of particle sizes. It can, however, be advantageous to specify values below the explosive concentration, for example, early warning thresholds of 90%, or 80% or 70% of the explosive dust concentration.

In addition, it is advantageous to specify maximum levels for changes in the increase of dust concentration (threshold slope (gradient) values), especially in the case of sudden sharp increases. A sudden sharp increase in dust concentration is measurable when a sudden leak or an isolated or complete rupture of the filter occurs. This is regarded as a malfunction and the filter is no longer capable of functioning.

It can be advantageous to use a combination of threshold concentration values and threshold values of the slope change to generate a malfunction signal.

A malfunction signal is generated whenever the exceeding of specified threshold value is measured and determined by the malfunction monitor sensor and the signal processing unit. This malfunction signal indicates that the filter is not functioning correctly. For the sake of simplicity, in the following sections the concepts malfunction signal from the malfunction monitoring sensor or filter monitoring unit are used to refer to analysis of signals and measurements from the malfunction sensor by a signal processing unit, in comparison with stored threshold values carried out by the signal processing unit, and generation of a malfunction signal by this unit.

If the filter is destroyed, a signal (malfunction signal) is generated by the malfunction monitoring sensor which initiates subsequent actions to prevent ingress of an aspirated air-dust mixture with elevated ignitable dust concentrations into the aspirating smoke detector system.

Under these conditions it is advantageous for the malfunction signal of the filter monitoring unit to switch off the aspirator in the aspirating smoke detector system or switch off the entire aspirating smoke detector system so that no more air is extracted from the enclosed environments being monitored. This shutdown prevents carry-over of a potentially explosive mixture into areas in which it could become an incalculable risk. In particular, the ingress of a combustible air-dust mixture into the aspirating smoke detector system is prevented. Electrical equipment such as aspirating smoke detector systems, which are not approved for use in ex-zones, could contain ignition sources such as ignition causing hot surfaces.

It is also advantageous for the length of the suction pipe between the filter and the entry into the aspirating smoke detector system to be calculated and measured in such a way that after the aspirator or the entire aspirating smoke detector system is switched off the transport velocity of the aspirated air-dust mixture in the suction pipe is reduced to 0 m/s prior to entry into the aspirating smoke detector system. This prevents ingress of an explosive atmosphere into the aspirating smoke detector system.

It is also advantageous for the malfunction signal of the signal processing unit to control one or several flaps and/or one or several valves which prevent the aspirated air-dust mixture from entering the aspirating smoke detector system. A convenient structural measure in this regard is to install a valve or flap which isolates the aspirating smoke detector system from the suction pipe in terms of air flow and/or diverts the aspirated air-dust mixture from the suction pipe into the surroundings or a container. A 3/2-way valve can be installed.

In an additional design variant of the method the signal from the malfunction monitoring sensor controls a flap or valve through which the aspirated air-dust mixture is diluted by adding uncontaminated air, or the explosive threshold in the enclosed environment of the aspirating smoke detector is reduced by mixing in an inerting gas, allowing ongoing detection of burning characteristics.

It can be advantageous to combine diversion of the aspirated air-gas mixture and/or the closing off of the entry to the suction pipe into the aspirating smoke detector system with the unit shutdown.

It can also be advantageous to integrate the flap or valve into the filter monitoring unit, which can be exchangeable.

A person skilled in the art can conceive of various reasons for detecting instances where a dangerous concentration level has been exceeded. Only a few instances are specified here.

The process mostly involves measurement methods whose values are compared with each other over time and where deviations are the primary signal for the malfunction monitoring sensor. The malfunction monitoring sensor is the device that turns a deviation of a measured value into a response.

It is advantageous to monitor the dust concentration in the gas stream by means of a light transmission or scattered light system. The light transmission or light dispersion system can be carried out using UV light, visible light, or IR beams. To maintain functioning of the scattered light or light transmission system the devices can be automatically reset in the event of visible soiling.

It is also advantageous to clean the lens of the light transmission or scattered light system automatically. This can be done using, for example, an air flushing device.

It is also advantageous to monitor the dust concentration in the gas stream by means of a microwave system.

It is advantageous to fit the filter with a separator.

Another possible solution is to monitor the dust concentration in the gas stream by means of a separator which traps the dust which is present so that the amount of dust per unit of time can be monitored. If this is too high, a signal is generated, i.e., the malfunction monitoring sensor switches off the aspirator in the aspirating smoke detector system and/or the entire detection system. The amount of dust behind the filter can be determined by weighing it or optically by means of a liquid level indicator or laser measurement of the level.

Another possibility for measuring the dust concentration in the gas stream involves installing an electrostatic monitoring unit.

It is also advantageous to separate out liquid from the air-dust mixture using a filtering procedure or by means of a separator.

It is also advantageous to return the filtered air-dust mixture to the closed environments for combustible materials.

In addition, it is advantageous if the sensor for detecting burning characteristics is connected to an alarm and/or a fire extinguishing system so that the fire can be extinguished immediately.

The solution proposed in the present disclosure has the advantage that enclosed environments such as material warehouses, silos, or bunkers for combustible materials which are subject to explosion prevention regulations can be monitored for typical fire criteria without the maximum possible concentration for an explosive atmosphere being exceeded, because in this case the equipment is automatically shut down or alternative subsequent actions are implemented, so that no explosive air-gas mixture can enter the aspirating smoke detector system. As a result, fire detection is possible in enclosed environments which are subject to explosion prevention regulations using low-cost standard components which are not approved for use in potentially explosive areas.

In the following sections, the present disclosure will be presented in greater detail by means of an implementation example.

DRAWINGS

The figures show:

DETAILED DESCRIPTION

Figure 1:
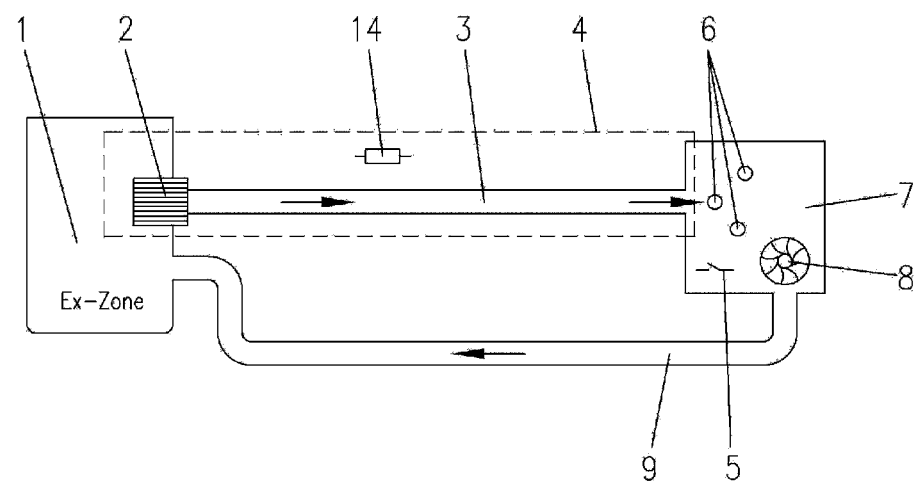
FIG. 1 is a schematic presentation of fire detection in an ex-zone.

FIG. 1 shows a storage area (1) with combustible dust, which represents a silo with a filter (2) on it. This could be, for instance, a silo for wood chips, wood pellets, wood shavings, grain, feed, fertilizer, or other materials.

The filter (2) separates the ex-zone from the non-ex-zone. It ensures, for example, in the case of storage or transport of wood particles (wood chips, wood pellets, wood shavings, and similar materials) a concentration of, for example, 30 g of wood dust per cubic meter for a particular range of particle sizes is not exceeded. Detection of a failure of function of the filter (2) as a result of damage or puncturing which could result in exceeding the ignition limit of the aspirated air-dust mixture must be guaranteed. For this reason the filter (2) is monitored by the filter monitoring unit (4), which contains a malfunction monitoring sensor (14) and a signal processing unit (not shown).

The air-dust mixture is aspirated via the filter (2) and the suction pipe (3) through the aspirator (8), which is located in the aspirating smoke detector system (7). In order to ascertain burning characteristics one or more sensors (6) for detecting burning characteristics are mounted in the aspirating smoke detector system (7). In the present case, there are three different sensors (6) which detect different burning characteristics. The air-dust mixture being monitored is led back into the storage area (1) for combustible dust by means of an air flow return pipe (9). To the extent required by pressure conditions, by implementing additional appropriate measures such as non-return valves, the direction of flow from the aspirating smoke detector system (7) to the storage area (1) can be ensured (not illustrated).

A fire alarm is set off as soon as burning characteristics are detected by one or more sensors (6).

Figure 3:
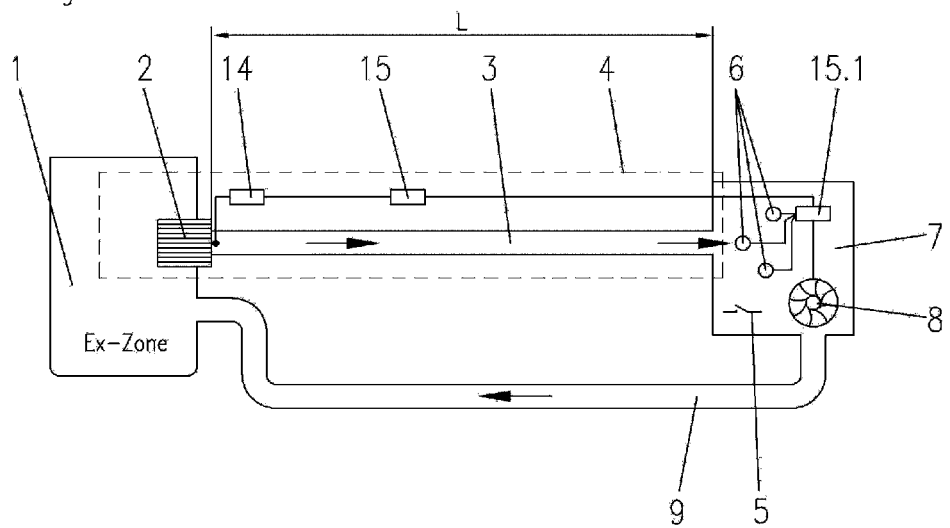
FIG. 3 is a schematic presentation of fire detection in an ex-zone with the malfunction monitoring sensor and the signal processing unit.

In this configuration given as an example the entry opening of the suction pipe (3) is directly connected with the filter (2). It is advantageous to position the malfunction monitoring sensor (14) directly at the filter (2) in the aspirated air-dust mixture in the suction pipe (3), as shown in FIG. 3.

Figure 2:
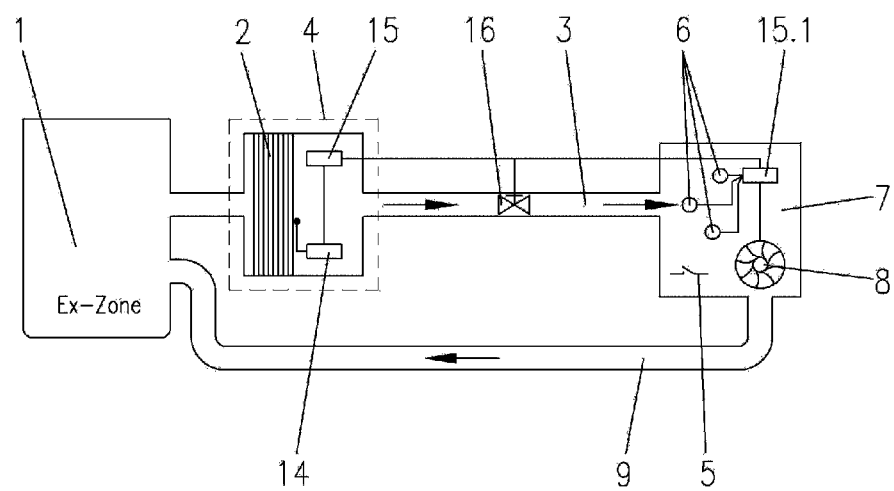
FIG. 2 is a schematic presentation of a device for fire detection in an ex-zone with a filter monitoring unit with a malfunction monitoring sensor and a valve for shutting off the air flow to the aspirating smoke detector system.

In an additional advantageous configuration, the filter (2) is located in the suction pipe (3) or in a separate filter monitoring unit (4) between the ex-zone and the aspirating smoke detector system (7) in the aspirated air flow, as shown in FIG. 2.

The filter (2) can be replaceable. Replacement of the entire filter monitoring unit (4) is also a configuration variant.

A significant feature of the invention is that as soon as the malfunction monitoring sensor (14) detects that, for instance, the filter (2) is not working because of damage or a leaky spot, action is taken to ensure that the air-dust mixture with increased dust concentration which may exceed the explosive limit cannot reach the sensors (6) and cannot enter the aspirating smoke detector system (7).

The malfunction monitoring sensor (14) is connected to the signal processing unit (15). This has threshold values stored for ignitable dust concentrations and/or warning threshold values and/or threshold slope values. In the configuration variants shown in FIG. 2 and FIG. 3 this signal processing unit (15) is mounted separately from the aspirating smoke detector system (7) in the filter monitoring unit (4).

However, it can also be advantageous that this function of the signal processing unit (15) is carried out by the signal processing unit (15.1) of the aspirating smoke detector system (7). This variant is not shown in the Figures.

The threshold value for an explosive wood dust concentration, for instance, is higher than 30 g of dust per cubic meter of air. It can, however, be advantageous to specify threshold values below the explosive concentration, for example, early warning thresholds of 90%, or 80% or 70% of the explosive dust concentration.

In a preferred configuration the malfunction signal is generated when 80% of the ignition limit value is measured in the aspirated air-dust mixture or a sudden rise of dust concentration is registered.

If the malfunction monitoring sensor (4) indicates that predetermined threshold values have been exceeded, the signal processing unit (15) generates a malfunction signal. This malfunction signal indicates loss of function of the filter (2).

FIG. 2 shows an advantageous configuration in which the malfunction monitoring sensor (14) and the signal processing unit (15), as well as the filter (2) are integrated into the filter monitoring unit (4) mentioned above.

If the filter (2) is destroyed, the malfunction signal triggers actions which prevent ingress of the aspirated air-dust mixture with elevated ignitable dust concentration into the aspirating smoke detector system (7).

In the configuration shown schematically in FIG. 2 the subsequent action in case of a malfunction is activation of a valve (16) such as a flap which seals off entry of air flow from the aspiration process into the aspirating smoke detector system (7).

FIG. 3 is a schematic presentation of a system with a malfunction monitoring sensor (4) and a signal monitoring unit (15) in which the malfunction signal from the signal processing unit (15) is transmitted to the signal processing unit (15.1) of the aspirating smoke detector system (7) and aspirator (8) and/or the entire aspirating smoke detector system (7) is shut down. As a result, the aspirated air-dust mixture, marked here with arrows, comes to a full stop.

Shutting down can be carried out by means of the switch (5) or other switching elements, or by means of a fire detection and control cabinet which receives a radio signal from the filter monitoring unit (4) (not shown). This reacts without delay by switching off the aspirator (8) and/or the entire aspirating smoke detector system (7) and reports the current state of the equipment to a process control unit (not shown).

After the shutdown the aspirator (8) and the aspirated air-dust mixture in the suction pipe (3) does not suddenly come to a stop. The shutdown time until the aspirator (8) has come to a full stop has to be taken into account. As a result, in this advantageous configuration (FIG. 3) the length L of the section of the suction pipe (3) between the filter (2) and the aspirating smoke detector system (7) is calculated in such a way that no ignitable atmosphere can enter the aspirating smoke detector system (7) during and after the shutdown procedure. The length L of this section of the suction pipe (3) is thus dependent on the transport velocity of the aspirated air-dust mixture and the time until the transport velocity is nearly 0 m/s. With this design length no aspirated air-dust mixture enters the aspirating smoke detector system (7).

With a transport velocity in the suction pipe of, for example, 1 m/s and a shutdown time of 5 s, this section of the suction pipe would have to have a length L of 5 m. The shutdown time is the period of time from the filter damage/filter rupture to cessation of transport of the aspirated air-dust mixture in the suction pipe (3). In this example it was assumed that the malfunction monitoring sensor (14) was located directly on the filter (2). If this malfunction monitoring sensor (14) is located at a given distance from the filter (2), the length of the section of the suction pipe (3) described above is increased by this distance. The length given above as an example is an estimate which assumes a constant velocity until the end of the shutdown time, i.e., until the aspirator comes to a full stop. In the case of more exact calculations the time dependence of the velocity $v(t)$ must be taken into account.

Figure 4:
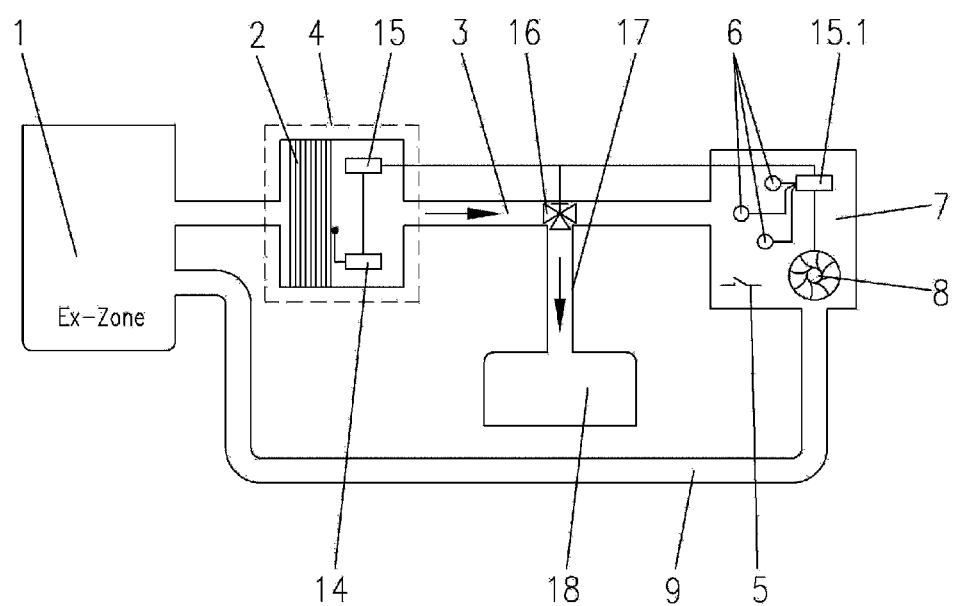
FIG. 4 is a schematic presentation of the device for fire detection in an ex-zone with a 3/2-way valve for shutting off the air flow to the aspirating smoke detector and simultaneous opening of a bypass line for diverting the aspirated air-gas mixture.

A further advantageous configuration in regard to subsequent action is shown in FIG. 4. Here the malfunction signal from the signal processing unit (15) controls one or several flaps and/or valves (16) which close the suction pipe (3) in the direction of the aspirating smoke detector system (7), and open a bypass pipe (17) or an emergency valve (not shown) for the aspirated air-dust mixture, and lead this into a container (18) or simply into the surrounding environment. This function can be implemented using two flaps/valves (16) or through a combined component such as a 3/2-way valve, as shown in FIG. 4. Activation of the flap/valve (16) prevents ingress of the aspirated air-dust mixture into the aspirating smoke detector system (7).

Figure 5:
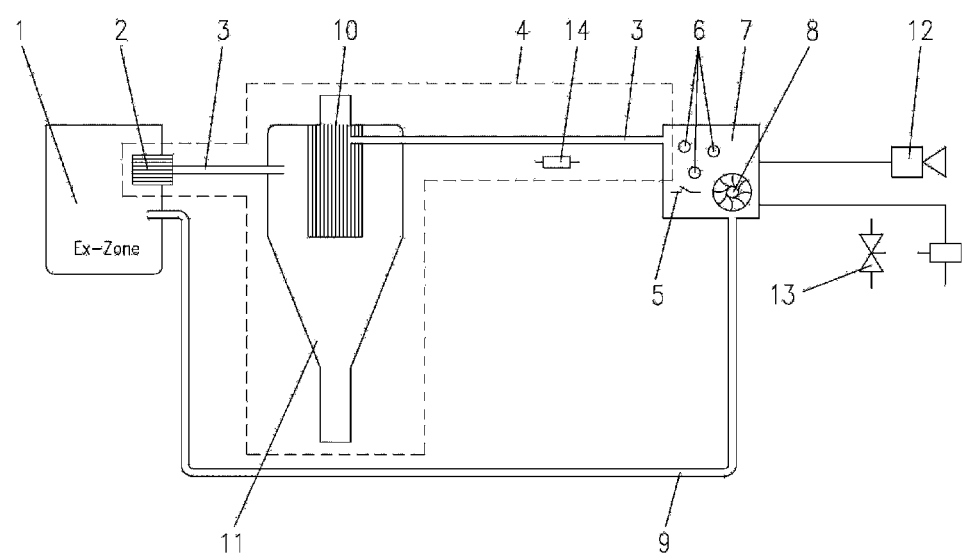
FIG. 5 is a schematic presentation of a device for fire detection with a separator and an alarm as well as a release valve for an extinguishing agent.

FIG. 5 demonstrates further development of the device from FIG. 1, which involves an additional filter (10) linked to a separator (11) between the storage area (1) for combustible materials and the aspirating smoke detector system (7). Here the filter monitoring system is supplemented by the additional specified components.

An alarm (12) such as a siren, a horn, or a fire detection and control cabinet is mounted behind the aspirating smoke detector system (7). Furthermore, in addition to the aspirating smoke detector system (7) a release valve for an extinguishing agent (13) with an appropriate fire extinguishing system is mounted, which is an advantageous configuration variant if upon identification of burning characteristics a fire is to be extinguished in the storage area (1) for combustible materials. When a fire is detected, this extinguishing agent release valve (13) is directly controlled by the aspirating smoke detector system (7) or by a fire detection and control cabinet to release the extinguishing agent.

Figure 6:
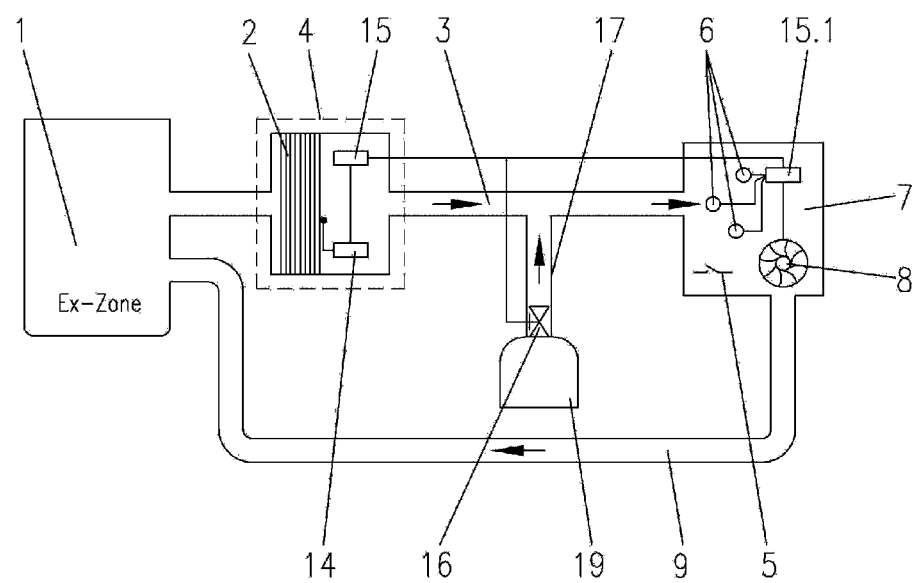
FIG. 6 is a schematic presentation of a device for fire detection in an ex-zone with a valve for opening a reservoir with an inerting gas.

A further configuration variant of the device in FIG. 1 is shown in FIG. 6. In this configuration a signal from the malfunction monitoring sensor (14) via the signal processing unit (15) activates a flap and/or valve (16). This valve opens a pressurized reservoir (19) containing inerting gas such as nitrogen. This is added to the aspirated air-dust mixture and thus reduces the explosive threshold in the enclosed environment of the aspirating smoke detector system (7). As a result, continued detection of burning characteristics is made possible.

Instead of inert gas, uncontaminated air from the ambient atmosphere can also be used with a pump to dilute the aspirated air-dust mixture.

List of reference signs used:
 Enclosed environments with potentially explosive atmospheres (ex-zone)/storage and transport areas for combustible materials with dust formation
 Filter
 Suction pipe
 Filter monitoring unit Switch/switch element
Sensor for detecting burning characteristics
Aspirating smoke detector system
Aspirator
Air flow return pipe
Filter B
Separator
Alarm device
Release valve for an extinguishing agent
Malfunction monitoring sensor
Signal processing and controlling unit of the malfunction monitoring sensor (14)
15.1 Signal processing and controlling unit of the aspirating smoke detector (7)
Flap/valve
Bypass line
Container
Reservoir with inerting gas
L Length of suction pipe (3)

The invention claimed is:

1. A method for detecting fires in enclosed environments (1) which are subject to regulations on prevention of explosions, out of which an air-dust mixture is filtered while the dust concentration in the air-dust mixture is reduced below the explosion threshold by means of filters (2) and the aspirated air-dust mixture checked for burning characteristics and, if necessary, a fire alarm activated, wherein:
the functioning of the filter (2) is monitored,
fire detection takes place outside ex-zones, using an aspirating smoke detector system (7) without an approval for use in areas where there is risk of explosion ex-zones, and
if the filter (2) is determined faulty, a signal processing unit (15, 15.1) of a malfunction monitoring sensor (14) generates a signal which triggers a subsequent action that prevents ingress of an aspirated air-dust mixture with an elevated dust concentration into the aspirating smoke detector system (7).

2. The method according to claim 1, wherein the signal of the signal processing unit (15, 15.1) of the malfunction monitoring sensor (14) shuts down at least one of the aspirator (8) and the aspirating smoke detector system (7).

3. The method according to claim 1, wherein the signal of the malfunction monitoring sensor (14) activates a valve (16) which prevents the ingress of the aspirated air-dust mixture into the aspirating smoke detector system (7).

4. The method according to claim 1, wherein the malfunction monitoring sensor (14) activates a flap and/or valve (16) which releases an additional volume of uncontaminated air or gas or an inerting gas, thus lowering the explosion threshold in the volume of the aspirating smoke detector system and enabling continued detection of burning characteristics.

5. The method according to claim 1, wherein at least one of pressure change over the filter (2) and the dust concentration in the flow gas can be integrated as disturbance monitoring.

6. The method according to claim 1, wherein the dust concentration of the gas stream is monitored by at least one of a light transmission measurement system and a scattered light measurement system.

7. The method according to claim 1, wherein the dust concentration of the gas stream is monitored by a microwave system.

8. The method according to claim 1, wherein the dust concentration of the gas stream is separated by a separator and the accumulated dust is weighed or its volume measured so that the filter system is monitored in relation to the air stream and the amount of accumulated dust per time unit.

9. A device for fire detection for use in enclosed environments (1) which are subject to regulations on prevention of explosions from which an air-dust mixture is extracted, filtered, checked for criteria typical of fires and if required a fire signal is triggered, comprising:
an aspirating smoke detector system (7) not having ex-approval and is located outside an ex-zone of the enclosed environment;
a suction pipe (3) between a filter (2) and the aspirating smoke detector system (7) wherein the filter (2) lowers the dust load of the aspirated air-dust mixtures from the enclosed environment (1) below the explosion level;
a filter monitoring unit (4) with a malfunction monitoring sensor (14); and
a first signal processing unit which processes the signals of the malfunction monitoring sensor (14), and if the filter (2) is determined to be damaged, triggers subsequent actions to preventingress of aspirated air-dust mixtures with elevated dust concentrations into the aspirating smoke system (7).

10. The device according to claim 9, wherein the first signal processing unit for the filter monitoring unit (4) is located in the aspirating smoke detector system (7).

11. The device according to claim 9, wherein the first signal processing unit operates autonomously from the aspirating smoke detector system (7) and transmits the malfunction signal to a second signal processing unit of the aspirating smoke detector system (7), which shuts down at least one of an aspirator (8) and the entire aspirating smoke detector system (7).

12. The device according to claim 11, wherein the second signal processing unit of the aspirating smoke detector system (7) processes signals from the malfunction monitoring sensor (14) and shuts down at least one of an aspirator (8) and the aspirating smoke detector system (7) in the event of the filter (2) being determined to be damaged.

13. The device according to claim 9, wherein a suction pipe (3) between the filter (2) and the entry into the aspirating smoke detector system (7) is designed in such a way that the transport velocity of the aspirated air-dust mixture in the suction pipe (3) is reduced to 0 m/s prior to entering the aspirating smoke detector system (7).

14. The device according to claim 9, wherein a valve is mounted in front of the aspirating smoke detector system (7) to preventingress of the aspirated air-dust mixture with elevated dust concentration into the aspirating smoke detector system (7).

15. The device according to claim 9, wherein behind the filter (2) an controllable valve (16) is installed for the introduction of one of an uncontaminated air, gas, or inerting gas which is mixed in with the air-dust mixture in a suction pipe (3) upstream of said aspirating smoke detector system.

* * * * *